United States Patent [19]
Cheung

[11] Patent Number: 5,298,969
[45] Date of Patent: * Mar. 29, 1994

[54] COMBINED OPTICAL TRAIN FOR LASER SPECTROSCOPY

[75] Inventor: H. Michael Cheung, Boston Heights, Ohio

[73] Assignee: The University of Akron, Akron, Ohio

[*] Notice: The portion of the term of this patent subsequent to Jul. 2, 2008 has been disclaimed.

[21] Appl. No.: 723,853

[22] Filed: Jul. 1, 1991

Related U.S. Application Data

[63] Continuation-in-part of Ser. No. 403,096, Sep. 5, 1989, Pat. No. 5,028,135.

[51] Int. Cl.$^5$ ............................................. G01N 21/00
[52] U.S. Cl. ..................................... 356/340; 356/343; 359/740; 250/574
[58] Field of Search .......................... 356/335–343; 250/574, 565, 524; 359/811, 819, 739, 740

[56] References Cited

U.S. PATENT DOCUMENTS

| | | | |
|---|---|---|---|
| 3,310,680 | 3/1967 | Hasegawa | 356/341 |
| 4,017,186 | 4/1977 | Shofner et al. | 356/342 |
| 4,027,973 | 6/1977 | Kaye | 356/338 |
| 4,037,965 | 7/1977 | Weiss | 356/336 |
| 4,176,960 | 12/1979 | Ecubreth | 356/338 |
| 4,242,194 | 12/1980 | Steiner | 204/299 R |
| 4,676,641 | 6/1987 | Bott | 356/336 |
| 4,764,013 | 8/1988 | Johnston | 356/349 |
| 5,028,135 | 7/1991 | Cheung | 356/340 |

Primary Examiner—Richard A. Rosenberger
Assistant Examiner—Hoa Q. Pham
Attorney, Agent, or Firm—Oldham, Oldham & Wilson Co.

[57] ABSTRACT

An improved method of collecting quasi-elastic light scattering (also known as QELS) data and time-average intensity simultaneously is disclosed, as is a novel apparatus therefor. The apparatus utilizes a novel optical element having a pair of diametrically aligned slits on a masking disc that eliminates the need of index matching fluids that are currently required to eliminate flare from the sample cell walls at the cell-sample and the cell-air interfaces. The novel optical element allows improved angular resolution and on-axis resolution for the fluctuation data obtained.

15 Claims, 5 Drawing Sheets

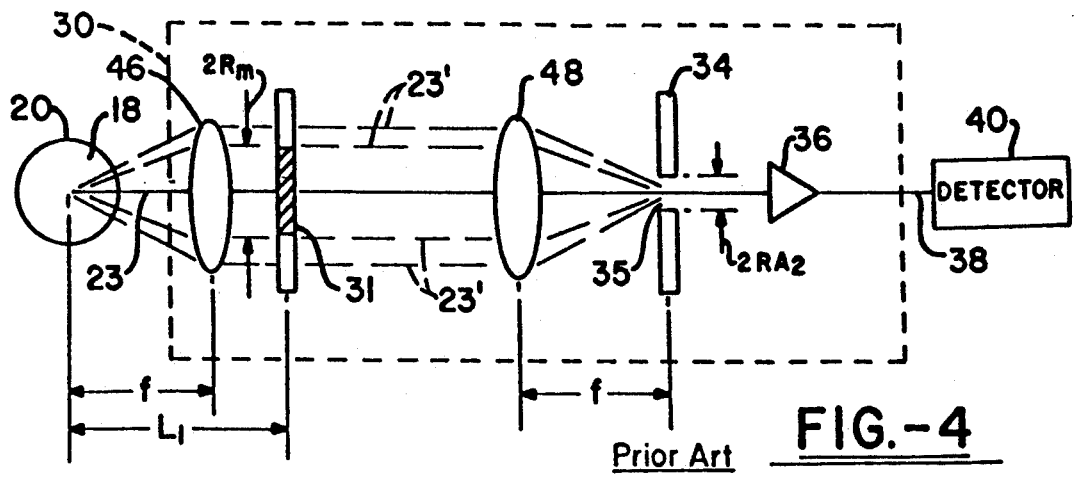
FIG.-4 Prior Art
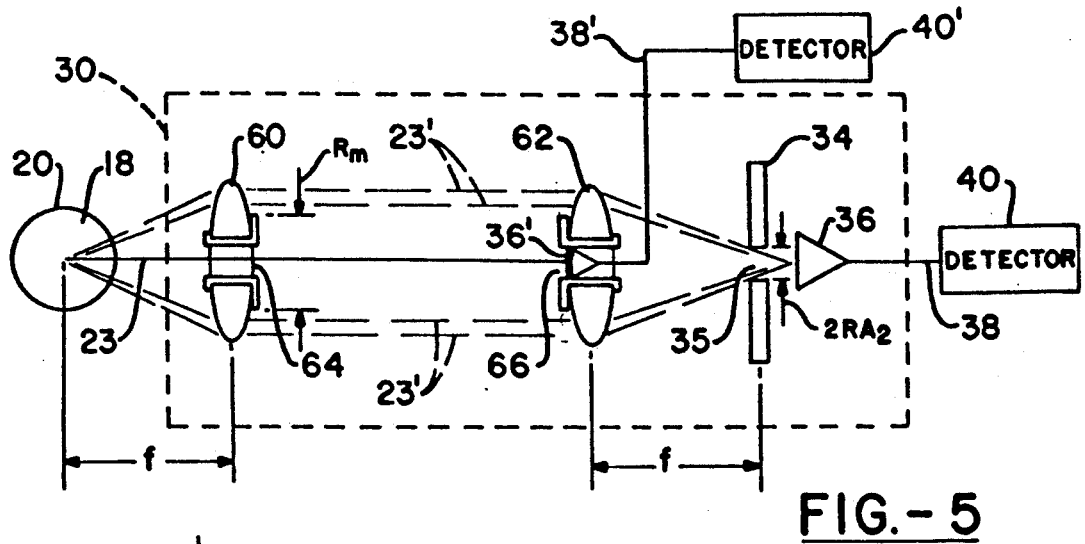
FIG.-5
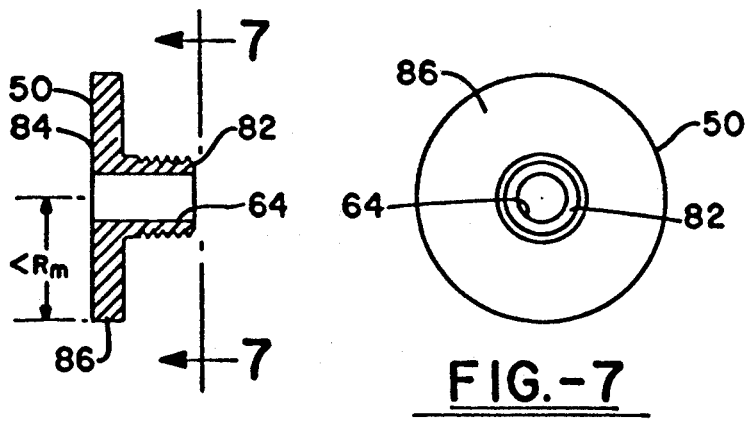
FIG.-6
FIG.-7

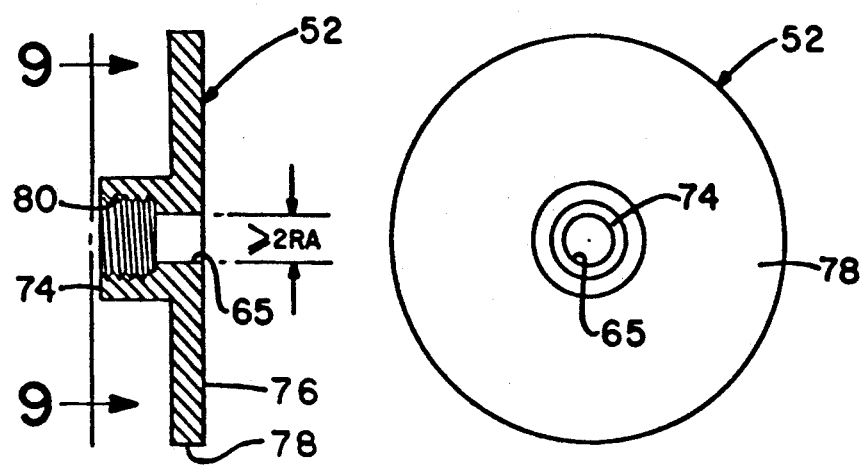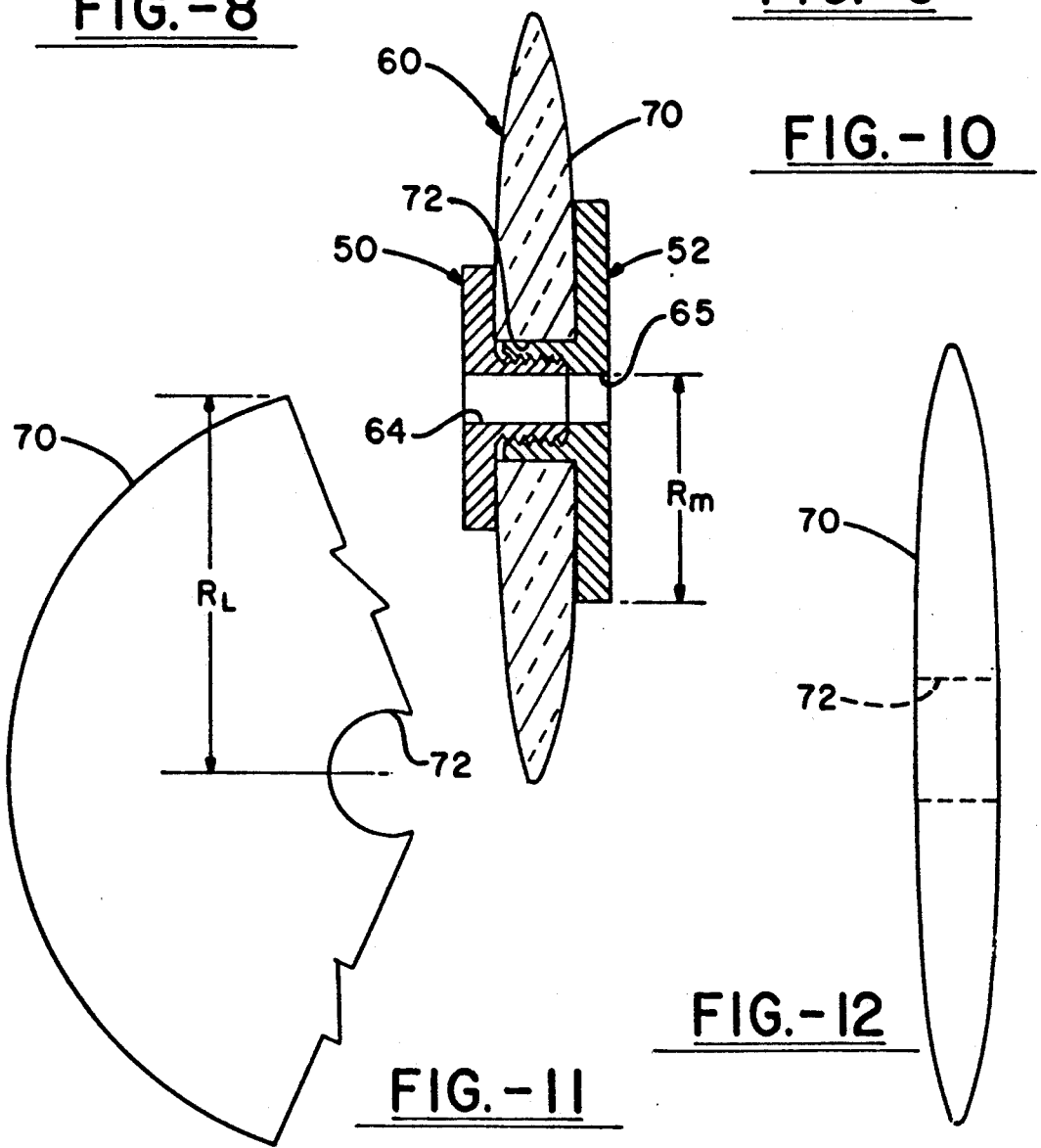

COMBINED OPTICAL TRAIN FOR LASER SPECTROSCOPY

This is a continuation-in-part of copending application Ser. No. 07/403,096 filed on Sep. 5, 1989 scheduled to issue as U.S. Pat. No. 5,028,135 on Jul. 2, 1991.

The present invention relates to an improved apparatus used for collecting quasi-elastic light scattering (also known as QELS) data and a method of use of such apparatus. More specifically, it relates to a method of increasing both the spatial resolution and angular resolution obtained by utilizing a pair of novel optical elements for collecting these data. To that extent, it provides an improvement over my co-pending application. Even more specifically, it relates to a novel optical element that eliminates the need of index matching fluids that are currently required to eliminate flare from the sample cell walls at the cell-sample and the cell-air interfaces.

DISCUSSION OF THE BACKGROUND ART

Light scattering experiments, particularly laser light scattering experiments, are commonly employed for measuring properties of certain physical systems such as solutions, microemulsions, micellar solutions, and colloidal dispersions. One common goal is to obtain data such as particle size, based upon diffusion coefficients. In measuring the scattering of laser light from such a physical system, it is important to measure not only the total (also referred to as "time-average" or "K-vector") intensity of the light scattered at a given fixed angle $\theta$, but it is also important to measure the intensity fluctuations of the light with time. The object of this invention and, indeed, other research, is to provide a single apparatus that can simultaneously attain both pieces of data.

The difficulty encountered in making both measurements simultaneously is that the gathering of total intensity data requires a very precise determination of the angle of scattering $\theta$, while the accurate collection of the intensity fluctuation data requires only a relatively accurate determination of $\theta$, but requires a very precise determination of the spatial resolution, that is, knowing exactly where in the sample plane the measurement is being made. This requirement for high spatial resolution arises from the fact that the observed intensity fluctuations observed arise from two different sources. The first source is called "homodyning" and is the interaction or interference caused by the scattering of light from separate particles in the physical system. This effect is the effect of interest to the researcher. The second source of fluctuations is called "heterodyning". It arises from light scattering at the wall of the sample holder, both at the wall-air interface and the wall-sample interface. Even a small error due to heterodyning can grossly affect the results in measuring fluctuation, although the net effect upon total intensity results is minimal.

The commonly accepted method of eliminating heterodyning effects is to immerse the sample cell in a liquid that has the same refractive index as the sample cell itself. This is referred to as use of an index-matching fluid. When the sample cell is constructed of glass, which is the most common case, the liquid of choice is toluene, which has recently come under intense scrutiny due to detrimental health effects. These effects are especially intolerable in a closed environment, as one would encounter in a space vehicle such as the space shuttle. Therefore, a method for obtaining the two distinct measures simultaneously using a single apparatus and not requiring a liquid such as toluene would be extremely beneficial for use in space applications.

A second, and not as common, method of eliminating heterodyning effects on the wall surfaces is to place an opaque mask in the middle portion of the optical train between two lenses used to focus and then refocus the image. Using such masks creates "dead zones" in the image which can be used to eliminate scattering from the walls of the sample cell. Although opaque masks are very effective when used in the center portion of the lens train, the best data point for collecting total intensity, that is, the line of light that passes directly through the middle of each lens on the light axis, becomes, unfortunately, unavailable, since it has been blocked by the opaque mask.

Another method of obtaining both pieces of data, that is, both total and fluctuation intensities, without use of an index matching fluid, is to use two separate optical trains. The obvious disadvantage to the researcher in this case is that the data are not simultaneously obtained, and inaccuracies due to changes in the light source, the sample, the angular position of the optical train, or other changes, are inevitably introduced.

SUMMARY OF THE INVENTION

A first object of the invention is to provide a novel optical element that can effectively mask certain light fluctuations arising from heterodyning by providing high spatial resolution without eliminating the "through the center" light data.

A second object of the invention is to provide a novel optical element that provides high spatial resolution without the use of index matching fluids, particularly hazardous liquids such as toluene.

A third object of the invention is to provide a single optical train employing a pair of the matched optical elements capable of collecting both total and fluctuation light intensities from a sample cell simultaneously.

A fourth object of the invention is to provide an optical system that can achieve the above objective without use of index matching fluids such as toluene.

A fifth object of the invention is to provide a method for simultaneously collecting total and fluctuation light data by use of a single optical train utilizing a pair of novel optical elements and without the use of index matching fluids.

These and other objects of the invention are achieved by a novel optical element, an optical train containing the novel optical element and a method of using the optical train.

The optical element for selectively masking a light beam passing between a first and a second focusing lens comprises a generally flat disc of material that is opaque to the light beam and which has a radius $R_M$ extending outwardly from the center of the disc. This radius is at least at large as the radius of the first focusing lens. The flat disc further has two identical slits disposed symmetrically and radially outwardly from the center on a single diameter, one slit on each side of the center, each slit having a first end at a radius $R_1$ from the center and a second end at a radius $R_2$ from the center, $R_2$ being larger than $R_1$. Each said slit also has a width w. The optical element may further have an eccentrically centered aperture, located on a diameter of the disc that is perpendicular to the diameter on which said slits are disposed. It may also have an concentrically positioned aperture with radius less than $R_1$. Such a central aperture may be contain a light detecting means, such as a photomultiplier tube or a photodiode. An optical element of this type may be attached to the first focusing lens, the second focusing lens, or both.

The optical train is designed for simultaneously measuring the intensity and fluctuations of a light bean scattered by a sample contained in a sample cell where the train is disposed upon a base to move smoothly in an arc coplanar to the scattered light beam and receive the light beam along a longitudinal axis thereof. The train comprises, in this order (from the end of the train which receives the scattered light beam): a first focusing lens having a radius $R_L$ and focal length f; a novel optical element as described above; a second focusing lens, having a radius at least as large as $R_L$ and a focal length f'; an aperture element comprising an opaque plate with an aperture of radius $R_A$ bored concentrically therethrough; first light detecting means; and first light analyzing means. The first focusing lens, novel optical element, second focusing lens, aperture element and first light detecting means are positioned colinearly upon the base along the axis of the scattered light beam, such that each is centered upon the light beam, the first focusing lens being located one focal length f from the center of the sample cell, the novel optical element being between said first and second focusing lenses, the second focusing lens being one focal length f' ahead of the aperture element, and the first light detecting means being proximate to the aperture element. The first light detecting means is communicated to the first analyzing means by electrical wiring means, irrelevant of whether the first analyzing means is disposed upon the base. In one embodiment, the first and second focusing lenses are identical in radius $R_L$ and focal length f. In an additional embodiment the novel optical element further has an eccentrically centered aperture, particularly one located on a diameter of the disc that is perpendicular to the diameter on which the slits are disposed. In another embodiment, the disc has an aperture of radius less than $R_1$ centered at the center of the disc. It is also possible to position a second light detecting means in the central aperture. This second light detecting means may be communicated to a second analyzing means by electrical wiring means, irrelevant of whether said second analyzing means is disposed upon the base. The novel optical element may be attached to the first focusing lens, the second focusing lens, or both.

A method for simultaneously acquiring total intensity and fluctuation light scattering data by using the novel optical train comprises: causing a light beam to be emitted from a light source and to pass into a sample contained within a sample cell; aligning the novel optical train described above and having first and second light detecting means, at a fixed angle $\theta$ from the incident axis of the light beam; collecting simultaneously total intensity light data in the second light detecting means and fluctuation light data in the first light detecting means; communicating simultaneously the total intensity light data and the fluctuation light data via electrical wiring means to respective second and first light analyzing means; and analyzing simultaneously the total intensity light data and the fluctuation light data in the respective second and first light analyzing means. Particular interest is in use of a laser light source, and use of the method with a sample cell wherein no index matching fluid is used with the sample cell. A particular method of interest is where the novel optical element has an eccentric aperture located on a diameter of the disc that is perpendicular to the diameter on which the slits are disposed and through which the light beam is directed outwardly through the first focusing lens to the sample cell, so that the fixed angle $\theta$ is near 180°.

An alternative method for acquiring fluctuation light scattering data at an angle $\theta$ of 180° comprises: aligning a novel optical train as described above and having first detecting means, with a sample contained within a sample cell; causing a light bean to be emitted from a light source positioned in the central aperture of the novel optical element to pass outwardly of the optical train into the sample. This results in some of the light being backscattered at an angle of 180° into the optical train, where the backscattered light is collected as fluctuation light data in the first light detecting means, communicated via electrical wiring means to the first light analyzing means; and analyzed in the first light analyzing means.

BRIEF DESCRIPTION OF THE DRAWINGS

FIG. 4 is a depiction of the "double lens"-type of optical train;

FIG. 5 is a depiction of the optical train of the inventor's co-pending application;

FIG. 6 is a cross-section view of the first lens insert element of the inventor's co-pending application, which is also used in the present invention;

FIG. 7 is a top view of the first lens insert element of the inventor's co-pending application;

FIG. 8 is a cross-section view of the second lens insert element of the inventor's co-pending application;

FIG. 9 is a top view of the second lens insert element of the inventor's co-pending application;

FIG. 10 is a cross-section view of the first and second lens insert elements of the inventor's copending application, as engaged with a lens to form the novel optical element of that invention;

FIG. 11 is a plan view of a portion of the modified lens used to construct the novel optical element of the inventor's co-pending application;

FIG. 12 is a side view of the modified lens used to construct the novel optical element of the inventor's co-pending application;

DETAILED DESCRIPTION OF THE DRAWINGS

Figure 1:
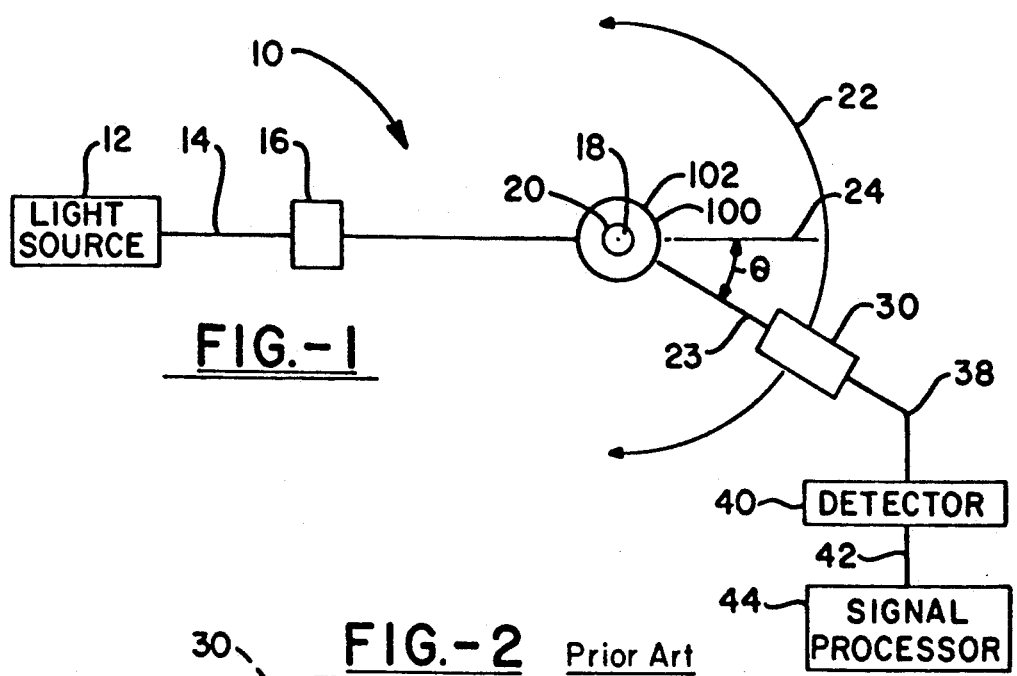
FIG. 1 is a general drawing of the apparatus used in light scattering spectroscopy, indicating the position of the optical train of this invention therein.

FIG. 1 shows the general layout of the optical apparatus 10 used to collect light scattering data from a sample 18, most commonly a liquid sample containing a physical system such as, for illustrative purposes only, a polymer solution, a microemulsion, a micellar solution or a colloidal suspension, contained within a sample cell 20. A light beam 14 is generated by a light source 12, preferably a source of monochromatic and coherent light, such as that obtained from a laser of the sort conventionally available. The light beam 14 may be passed through a conditioning train 16, wherein the beam is collimated, polarized, or otherwise conditioned for passage through the sample cell 20. Conditioning means of this sort are well known and obvious to those skilled in this art.

An optical train 30, the exact details of which are disclosed later, but which generally contains means for conditioning and receiving a scattered light beam 23 of the sort as light beam 14, is disposed at an angle $\theta$ from the incident axis 24 of the light beam, although the optical train 30 is disposed so as to be able to pivot along a planar arc 22 about the center of the sample so that the angle $\theta$ may be varied from 0° to almost 180°, although it will be readily apparent that the approach to an angle of 180° will be limited by the size of the optical train 30 and its interference with the incident light beam 14.

Optical train 30 is connected by conventional electrical means 38 to analyzing means 40, which is sequentially connected by conventional electrical means 42 to a signal processing means 44. In this manner, which is well known in the art, the intensity of the scattered light beam 23 may be measured and recorded.

In one known method for obtaining the desired fluctuation data, the sample cell 20 is enveloped by an optional cell 100, said optional cell containing a fluid 102 with an index of refraction close to that of the wall of sample cell 20. This method would commonly use the optical train 30 disclosed in FIG. 2 to collect the fluctuation data.

In a second known method for obtaining the desired fluctuation data, the optional cell 100 and fluid 102 are not utilized, but total intensity data and intensity fluctuation data are not collected simultaneously. The former are collected with an optical train 30 as disclosed in FIG. 2 and the latter are collected with an optical train 30 as disclosed in FIG. 3 or FIG. 4.

In the method of this invention for collecting total and fluctuation intensity data simultaneously, the optional cell 100 and fluid 102 are not used. One such optical train 30 is disclosed in the inventor's co-pending application and shown herein as FIG. 5. The optical train used in the -method of the present invention is the optical train disclosed in FIG. 13 and described further below.

Figure 2:
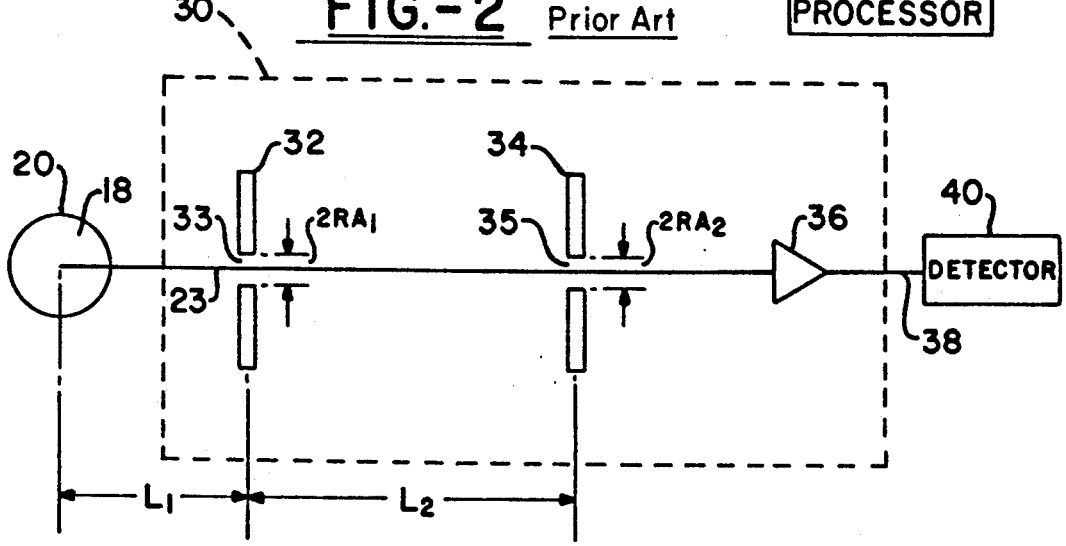
FIG. 2 is a depiction of the "double pinhole"-type of optical train of the prior art.

Referring now to FIG. 2, the "double-pinhole" type of optical train 30 is disclosed. This type of optical train is well known in the prior art. The scattered light beam 23 originates within the sample 18, which sample is contained in the sample cell 20. Optical train 30 is aligned with the scattered light beam 23 such that, at a distance $L_1$ from the origin of the scattered beam, the beam encounters a first aperture element 32. This aperture element, comprising material that is opaque to the electromagnetic energy of scattered light bean 23, has an aperture 33, of radius $RA_1$, located centrally therein.

A second aperture element 34 is located colinearly along light beam 23 and at a distance $L_2$ further from the light source than first aperture element 32. Second aperture element 34, also opaque to light beam 23, has an central aperture 35, of radius $RA_2$, disposed therein. Also colinear with light beam 23 is a light detection means 36, preferably a photodiode or photomultiplier tube (PMT), either of which are conventional, and either of which are used to gather electromagnetic energy in the form of photons and convert said energy into a electrical impulse. Such an impulse can be passed via conventional electrical wiring 38 to a light analyzing means 40 for further analysis.

Such a "double-pinhole" system is ideal for providing a very exact angular resolution, since only light that originates along or very close to the light beam 23 can reach the light detection means 36, and the cross-axis resolution, which is the spatial selectivity of the optical train on an axis perpendicular to the light beam 23, can be made arbitrarily small by adjusting the sizes of $RA_1$, $RA_2$, $L_1$, and $L_2$. In fact, the double-pinhole system has an angular resolution which cannot be matched by any system that contains lenses. Unfortunately, it is also abundantly obvious that any light that originates along the axis of the light beam 23 and surrounding cross-axis resolution will reach the detection means 36, so this system is said to have no "on-axis" resolution, and the data obtained are useless by themselves to eliminate the heterodyning effects of the walls.

An ideal optical train will measure total intensity by use of the "double-pinhole" method.

Figure 3:
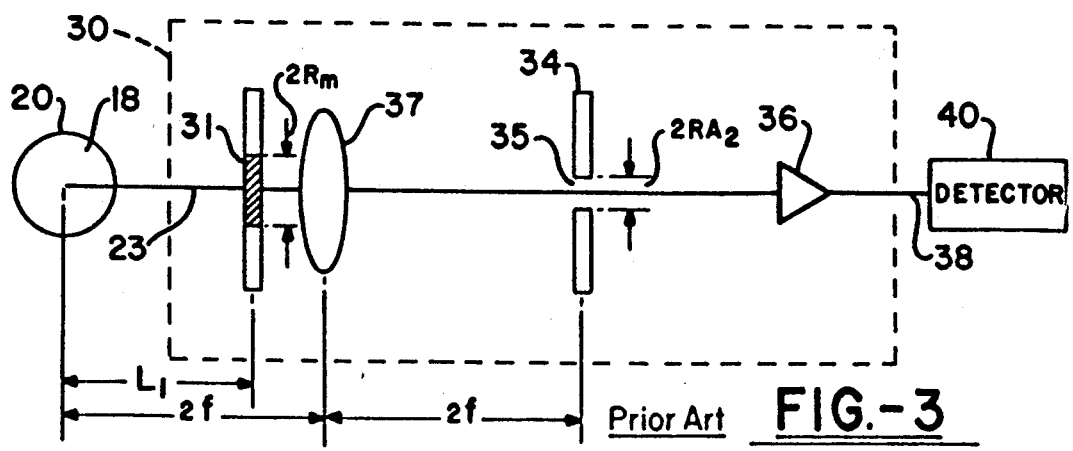
FIG. 3 is a depiction of the "single lens"-type of optical train of the prior art.

Referring now to FIG. 3, an alternate optical train, the "single-lens" system, known in the prior art is disclosed. The scattered light bean 23 originates within the sample 18, which sample is contained in the sample cell 20. Optical train 30 is aligned with the scattered light beam 23 such that, at a distance $L_1$ from the origin of the scattered beam, the beam encounters an optional opaque masking element 31 of radius $R_m$ at a distance $L_1$ from the source. This masking element prevents direct passage of "on axis" light through the optical train. Certain light can, however, enter a focusing lens 37, located at a distance twice the focal length f of the lens from the source, and any such light will be focused on a point colinear with the source and at a distance two focal lengths farther along the light axis 23 from the lens 37. An aperture element 34 is located colinearly along light beam 23 and such a distance 2f from the lens 37. The aperture element 34, also opaque to light beam 23, has an central aperture 35, of radius $RA_2$, disposed therein, and it serves to cut out extrinsic light not originating at the light source. Also colinear with light beam 23 is a light detection means 36, preferably a photodiode or photomultiplier tube (PMT), either of which are conventional, and either of which are used to gather electromagnetic energy in the form of photons and convert said energy into a electrical impulse. Such an impulse can be passed via conventional electrical wiring to a light analyzing means 40 for further analysis.

In terms of "on axis" resolution, the single lens system offers no improvement over the double-pinhole design if no masking element 31 is used, since no light originating along the light beam axis 23 is excluded, and, in fact, the angular resolution decreases from the double-pinhole system. But a properly selected (using conventional and well known optics principles) center mask can begin to discriminate as to "on axis" light and provide the desired spatial resolution.

Referring now to FIG. 4, another alternate optical train 30, the "double lens" system, is disclosed. As with FIG. 2 and 3, the scattered light beam 23 originates within the sample 18, which sample is contained in the sample cell 20. Optical train 30 is aligned with the scattered light beam 23 such that the light beam 23 encounters a first lens 46 at a distance one focal length from the origin of the light scattering. Elementary optics requires that such light entering the lens will not refocus of itself, and will, instead, be split into a plurality of beams 23' parallel to light axis 23. At a distance $L_1$ from the scattering source, the plurality of beams engaunters an optional opaque masking element 31 of radius $R_m$ centered on the light axis 23. This masking element 31 will exclude all beams 23' from lens 46 that are closer than $R_m$ to the light axis 23. A second lens 48, with an identical focal length f to that of first lens 46, and located colinear to lens 46 will refocus the plurality of beaus 23' reaching it into a single point colinear with the source and at a distance one focal length f further along the light axis 23 from the lens 48. An aperture element 34 is located colinearly along light beam 23 and such a distance f from the lens 37. The aperture element 34, also opaque to light beam 23, has an central aperture 35, of radius $RA_2$, disposed therein, and it serves to cut out extrinsic light not originating at the light source. Also colinear with light beam 23 is a light detection means 36, preferably a photodiode or photomultiplier tube (PMT), either of which are conventional, and either of which are used to gather electromagnetic energy in the form of photons and convert said energy into a electrical impulse. Such an impulse can be passed via conventional electrical wiring to a light analyzing means 40 for further analysis.

This manner of optical train greatly improves the "on axis" resolution, but the angular uncertainty increases dramatically since by definition no light passing along light axis 23 can reach light detection means 36, making the double lens optical train quite undesirable for making total intensity measurements. As with the single lens system, the use of the center mask increases angular uncertainty, but the increased "on axis" spatial resolution more than compensates for the loss of angular certainty.

The optics of the dual lens system permit some optimization of the elements involved, and it can be shown that the preferred mask radius $R_m$ of mask element 31 is about 0.8 RL, where RL is the radius of lenses 46 and 48.

The optical train of my invention as described in co-pending application 07/403,096 is disclosed in FIG. 5. This invention incorporates the best elements of the double pinhole system with those of the dual lens system so as to allow simultaneous acquisition of total intensity data via the preferred double pinhole method and fluctuation data via the preferred dual lens method. In this manner, the prior art's need for indexing fluid is eliminated and a compact dual purpose optical train is facilitated.

As in the prior FIGURES, the scattered light beam 23 originates within the sample 18, which sample is contained in the sample cell 20. Optical train 30 is aligned with the scattered light beam 23 such that the light beam 23 encounters a first combined optical element 60 at a distance one focal length from the origin of the light scattering. The construction of this combined optical element 60 is described in more detail below, but suffice it to say for now that the combined optical element incorporates desirable aspects of a pinhole aperture, a lens and a mask element of radius $R_m$, that the pinhole aperture 64 is aligned with the light beam 23 and the mask element is positioned opposite the incident scattered light bean 23. Elementary optics requires that such light entering the lens aspect will not refocus of itself, and will, instead, be split into a plurality of beams 23' parallel to light axis 23. At a distance L from the scattering source, the plurality of beams 23' created by the lens aspect encounters a second combined optical element 62, the masking component of which, being disposed on the front face of the second combined optical element 62 and having radius RM centered on the light axis 23, excludes all beams from lens 46 that are closer than RM to the light axis 23. The lens aspect of the second combined optical element, having an identical radius RL and focal length f to that of the lens aspect of the first combined optical element 60 and being located colinear to the lens aspect of the first combined optical element will refocus the plurality of beams 23' reaching it into a single point colinear with the source and at a distance one focal length f further along the light axis 23 from the second combined optical element 62. An aperture element 34 is located colinearly along light beam 23 and such a distance f from the second combined optical element 62. The aperture element 34, also opaque to light beam 23, has an central aperture 35, of radius $RA_2$, disposed therein, and it serves to cut out extrinsic light not originating at the light source. Also colinear with light beam 23 is a first light detection means 36, preferably a photodiode or photomultiplier tube (PMT), either of which are conventional, and either of which are used to gather electromagnetic energy in the form of photons and convert said energy into a electrical impulse. Such an impulse can be passed via a first conventional electrical wiring means 38 to a first light analyzing means 40 for further analysis.

The optical train of this embodiment offers, however, an alternative light path. The pinhole aspect 64 of the first combined optical element 60 permits light encountering it along the light beam axis 23 to pass directly through the optical element, as in the conventional pinhole aperture disclosed in FIG. 2. At a distance L from the first combined optical element 60, this light encounters the pinhole aspect 66 of the second combined optical element 62, which is colinear to the first combined optical element 60. Directly within the pinhole aspect 66 the light strikes a second light detection means 36' preferably a photodiode or photomultiplier tube (PMT), either of which are conventional, and either of which are used to gather electromagnetic energy in the form of photons and convert said energy into a electrical impulse. Such an impulse can be passed via a second conventional electrical wiring means 38' to a second light analyzing means 40' for further analysis.

Once collected, the data from the first light analyzing means 40 are analyzed for the fluctuation characteristics of the sample and the data from the second light analyzing means 40' are analyzed for the total intensity characteristics of the sample. In this manner, simultaneous data acquisition is achieved.

FIGS. 6 through 12 reveal more descriptively the elements of the combined optical element 60 or 62 of the co-pending application.

FIG. 11 shows a plan view of a portion of a focusing lens 70 of the sort well known in the art, having focal length f and radius $R_L$. FIG. 12 shows a side view of the same lens. The lens 70 may be any sort of focusing lens, including convex-convex, plano-convex, achromatic, aspheric, or the like. When the lens 70 is used with the present invention, it may also be possible to use a cylindrical lens. A hole 72, small in diameter relative to lens radius $R_L$ but larger than twice the desired pinhole aperture RA is bored concentrically into the lens 70 by known conventional means.

As illustrated best in FIGS. 8 and 9, a first lens insert element 52 is prepared from a rigid material, opaque to light 23 of the sort used in the optical train 30. Preferably this material is metallic, but the exact selection of material will be obvious to one skilled in this art. The first lens insert element 52 is essentially a cylindrical solid having first and second ends 74 and 76, respectively, with a circular flanged portion 78 at the second end 76 thereof. The cylindrical portion of the first lens insert element 52 has an external diameter slightly smaller than the diameter of the hole 72 bored concentrically into the lens 70, thereby providing a close fit between the lens and the insert element. Starting at the first end 74 of the cylindrical portion, at least a significant part of the internal surface 80 of the cylindrical portion is adapted for engaging, preferably threadingly, the external surface of a second lens insert element, although it is not necessary that the threading extend the entire length thereof. The unthreaded portion of the internal surface, if any, has a diameter no smaller than 2 RA, the desired aperture radius for the aperture function which this element will perform. The circular flanged portion 78 is to function as the masking element, so it has a radius RM, and, in the preferred embodiment, this radius RM is sized to be about 0.8 RL, where RL is the radius of the lens wherein the insert element will be fitted.

As illustrated best in FIGS. 6 and 7, a second lens insert element 50 is also prepared from a rigid material, opaque to light 23 of the sort used in the optical train 30. This element should be manufactured from the same material as the first lens insert element 52. Preferably this material is metallic, but the exact selection of material will be obvious to one skilled in this art. The second lens insert element 50 is essentially a cylindrical solid having first and second ends, 82 and 84, respectively, with a circular flanged portion 86 at the second end 84 thereof. The cylindrical portion of the lens insert element 52 has an external diameter sized and adapted, for at least a portion of its length, beginning at its first end 82, to engage, preferably threadingly, the internal surface 80 of the first lens insert element 50. The internal diazieter of the cylindrical portion is 2 RA, as this opening 64 will function as the pinhole aperture in the combined optical element. The circular flanged portion 86 at the second end 84 of the cylindrical portion does not perform a masking function, so the radius of the flanged portion is not generally critical to the invention, but the flanged portion should have a radius no larger than $R_m$ and the flanged portion 86 should extend far enough beyond the cylindrical portion to secure and support the lens wherein the insert elements will be fitted.

As best shown in FIG. 10, when the first and second lens insert elements, 52 and 50, respectively, are engaged with each other by engaging their respective first ends 74 and 82 from opposite sides of the hole 72 bored in lens 70, the first and second insert elements 52 and 50 should engage each other enough that the flanged portions of each, 78 and 86, respectively, should closely approach the external surface of the lens 70, and slightly bear upon it.

Thus constructed, the lens 70 with lens insert elements 52 and 50 properly engaged therein constitutes the novel optical element of the invention that is illustrated as 60 and 62 in FIG. 5.

In addition to the embodiment presented in my co-pending application, there is at least one further manner of achieving the objects of the present invention. The optical train of this present invention is disclosed in FIG. 13, which is a schematic presentation of an optical train in the same manner of FIGS. 2-5. The present invention incorporates the best elements of the double pinhole system with those of the dual lens system so as to allow simultaneous acquisition of total intensity data via the preferred double pinhole method and fluctuation data via the preferred dual lens method. In this manner, the prior art's need for indexing fluid is eliminated and a compact dual purpose optical train is facilitated. Even further, the present invention offers some flexibility beyond that offered by my co-pending application. For example, the present invention enables the user to directly use the same optical train for back-scattering experiments in which $\theta$, as shown in FIG. 1, approaches 180°.

As in the prior figures, the scattered light beam 23 originates within the sample 18, which sample is contained in the sample cell 20. optical train 30 is aligned with the scattered light beam 23' such that the light beam 23 encounters a first combined optical element 200 of the present invention at a distance one focal length from the origin of the light scattering. The construction of this combined optical element 200 is described in more detail below, but suffice it to say for now that the combined optical element incorporates desirable aspects of a pinhole aperture, a lens and a masking element with a pair of slits for light passage, that the pinhole aperture 64 is aligned with the light beam 23 and that the mask element is positioned opposite the incident scattered light beam 23. Elementary optics requires that such light entering the lens aspect will not refocus of itself, and will, instead, be split into a plurality of beams 23' parallel to light axis 23. At a distance L from the scattering source, the plurality of beams 23' created by the lens aspect encounters a second combined optical element 202, the masking component of which, being disposed on the front face of the second combined optical element 202 and having a masking element with a pair of symmetric slits, the masking element being centered on the light axis 23, excludes all beams 23' from passage through the lens aspect that are closer to the light axis 23 than the slits. The lens aspect of the second combined optical element 202, preferably having an identical radius RL and focal length f to that of the lens aspect of the first combined optical element 200 and being located colinear to the lens aspect of the first combined optical element 200, will refocus the plurality of beams 23' reaching it into a single point colinear with the source and at a distance one focal length f further along the light axis 23 from the second combined optical element 202. It should be readily recognized that the lens aspect of the second optical element 202 could easily have a different radius or focal length. In fact, a different focal length may be quite desirable for advantageously positioning the optical train elements relative to the sample. These adjustments of focal length and lens radius are well within the knowledge of one of ordinary skill in optics. An aperture element 34 is located colinearly along light beam 23 and such a distance f from the second combined optical element 202. The aperture element 34, also opaque to light beam 23, has an central aperture 35, of radius $RA_2$, disposed therein, and it serves to cut out extrinsic light not originating at the light source. Also colinear with light beam 23 is a first light detection means 36, preferably a photodiode or photomultiplier tube (PMT), either of which are conventional, and either of which are used to gather electromagnetic energy in the form of photons and convert said energy into a electrical impulse. Such an impulse can be passed via a first conventional electrical wiring means 38 to a first light analyzing means 40 for further analysis.

The optical train of this invention offers, however, an alternative light path. The pinhole aspect 64 of the first combined optical element 200 permits light encountering it along the light beam axis 23 to pass directly through the optical element 200, as in the conventional pinhole aperture disclosed in FIG. 2. At a distance L from the first combined optical element 200, this light encounters the pinhole aspect 66 of the second combined optical element 202, which is colinear to the first combined optical element 200. Directly within the pinhole aspect 66 the light strikes a second light detection means 36', preferably a photodiode or photomultiplier tube (PMT), either of which are conventional, and either of which are used to gather electromagnetic energy in the form of photons and convert said energy into a electrical impulse. Such an impulse can be passed via a second conventional electrical wiring means 38' to a second light analyzing means 40' for further analysis.

Once collected, the data from the first light analyzing means 40 are analyzed for the fluctuation characteristics of the sample and the data from the second light analyzing means 40' are analyzed for the total intensity characteristics of the sample. In this manner, simultaneous data acquisition is achieved.

FIGS. 6, 7, 11, 12, 14 and 15 reveal more descriptively the elements of the combined optical element 200 or 202 of the present invention.

FIGS. 11 and 12, as described above, show the type of lens that would be useful with the combined optical element 200 or 202.

Figures 14, 15:
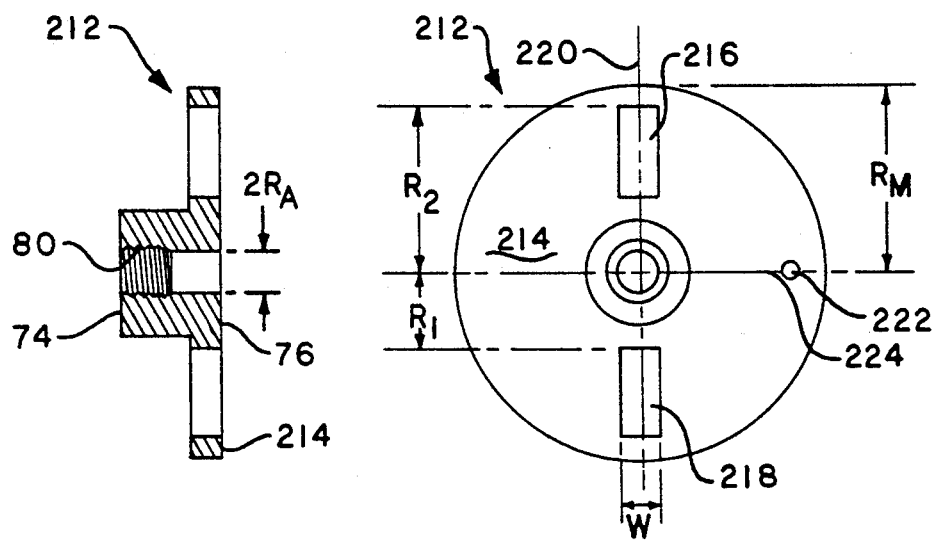
FIG. 14 is a cross-section view of the second piece of the optical masking element of the present invention, taken along diameter 220 of FIG. 15.
FIG. 15 is a front view of the second piece of the optical masking element of the present invention.

As illustrated best in FIGS. 14 and 15, a first lens insert element 212 is prepared from a rigid material, opaque to light 23 of the sort used in the optical train 30. Preferably this material is metallic, but the exact selection of material will be obvious to one skilled in this art. The first lens insert element 212 is essentially a cylindrical solid having first and second ends 74 and 76, respectively, with a circular flanged portion 214 at the second end 76 thereof. The cylindrical portion of the first lens insert element 212 has an external diameter slightly smaller than the diameter of the hole 72 bored concentrically into the lens 70, thereby providing a close fit between the lens and the insert element. Starting at the first end 74 of the cylindrical portion, at least a significant part of the internal surface 80 of the cylindrical portion is adapted for engaging, preferably threadingly, the external surface of a second lens insert element, although it is not necessary that the threading extend the entire length thereof. The unthreaded portion of the internal surface, if any, has a diameter no smaller than 2 RA, the desired aperture radius for the aperture function which this element will perform. The circular flanged portion 214 is to function as the masking element, so it has a radius RM, which is at least as large as RL where RL is the radius of the lens 70 wherein the insert element 212 will be fitted.

Figure 16:
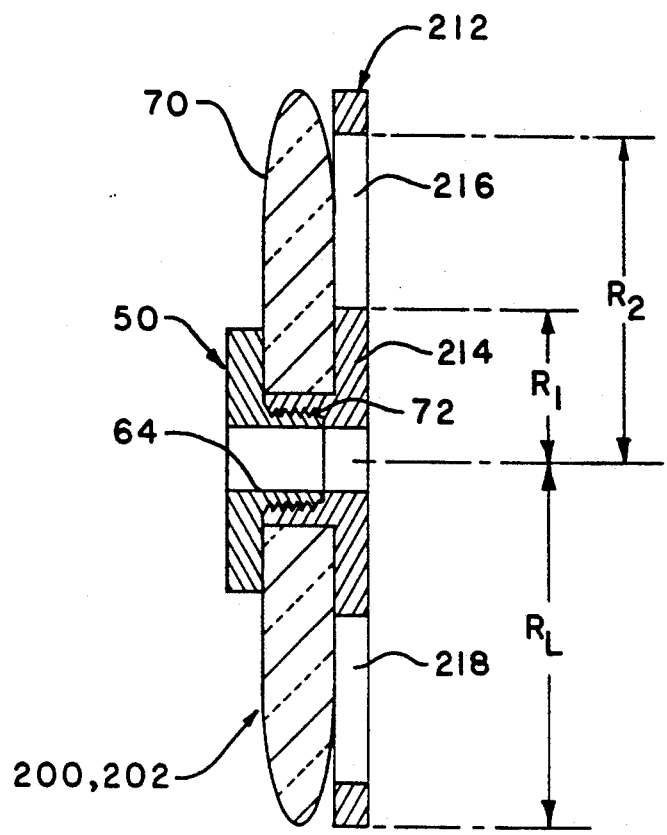
FIG. 16 is a cross-section view of the assembled optical masking element of the present invention, taken along diameter 220 from FIG. 15.

It will be appreciated that the circular flanged portion 214 will exclude all light passage if there are no further openings provided in it. Therefore, as shown in FIG. 16 a pair of essentially rectangular slits 216, 218 are symmetrically provided along a single diameter 220 of the flanged portion 214. The first end of each slit is disposed at a distance $R_1$ from the center of the flanged portion 214, so any light beam 23' closer than $R_1$ to the center will not pass through the lens 70. The second end of each slit is disposed at a distance $R_2$ from the center of flanged portion 214, so any light beam 23' farther than $R_2$ from the center will not pass through the lens 70. It will, of course, be understood that when $R_2$ is equal to RL, the respective slits 216 and 218 are essentially open rectangular channels. Each slit 216 and 218 also has a width dimension w associated with it, such that the slit 216 or 218 is symmetrically disposed along the diameter 220. In other words, each side of each slit 216 or 218 is located parallel to diameter 220 at a distance of w/2 from that diameter.

By placing the slits 216 and 218 on the flanged portion 214 in this manner, it may be shown from trigonometric calculations that the angular uncertainty, represented as $\Delta\theta$, may be described by the formula:

$$\Delta\theta = 2 \arctan(w/2f)$$

where w and f have the definitions ascribed above. Similarly, the on-axis resolution, represented as $\Delta z$, may be determined to be described by the formula:

$$\Delta z = RAf/R_1$$

where $R_1$ and f are features of the optical element as described above and RA is the radius of the receiving aperture 34.

It is noted that the embodiment shown in FIG. 15 also shows a small circular aperture 222 disposed on a diameter 224 that is perpendicular to diameter 220. This aperture 222 may be used to direct a light beam 14 from a light source 12, such as the laser, outwardly from the optical train 30 to the sample 18 and back, thereby effecting a backscattering experiment where $\theta$ approaches 180°. In this manner, the difficulty of allowing $\theta$ to approach 180°, as described in relation to FIG. 1, is overcome. It is noted that the positioning of aperture 222 on a perpendicular diameter is not critical to the operation of the aperture, but that it would probably constitute the most preferred positioning.

It will be readily apparent that, by centrally positioning the aperture 222 and using it for directing a light source 12 at a sample 18 in the manner of FIG. 1, the result is an optical train in which $\theta$ is equal to 180°. Although this eliminates the ability to collect total intensity data via the pinhole method, such is not viewed as a serious drawback, particularly since this new optical masking element permits an additional degree of angular resolution heretofore unknown in the art, even with the inventor's co-pending application.

The second lens insert element 50 has already been illustrated in FIGS. 6 and 7, and it is as readily useful with the present invention as with the inventor's co-pending application. Since flanged portion 86 does not perform a masking function, the radius of the flanged portion is not generally critical to the invention, but the flanged portion 86, in order to not interfere with the functioning of slits 216 and 218 in insert element 212, should have a radius no larger than $R_1$ and the flanged portion 86 should extend far enough beyond the cylindrical portion to secure and support the lens 70 wherein the insert elements will be fitted.

As best shown in FIG. 16, when the first and second lens insert elements, 212 and 50, respectively, are engaged with each other by engaging their respective first ends 74 and 82 from opposite sides of the hole 72 bored in lens 70, the first and second insert elements 52 and 50 should engage each other enough that the flanged portions of each, 78 and 86, respectively, should closely approach the external surface of the lens 70, and slightly bear upon it.

Figure 13:
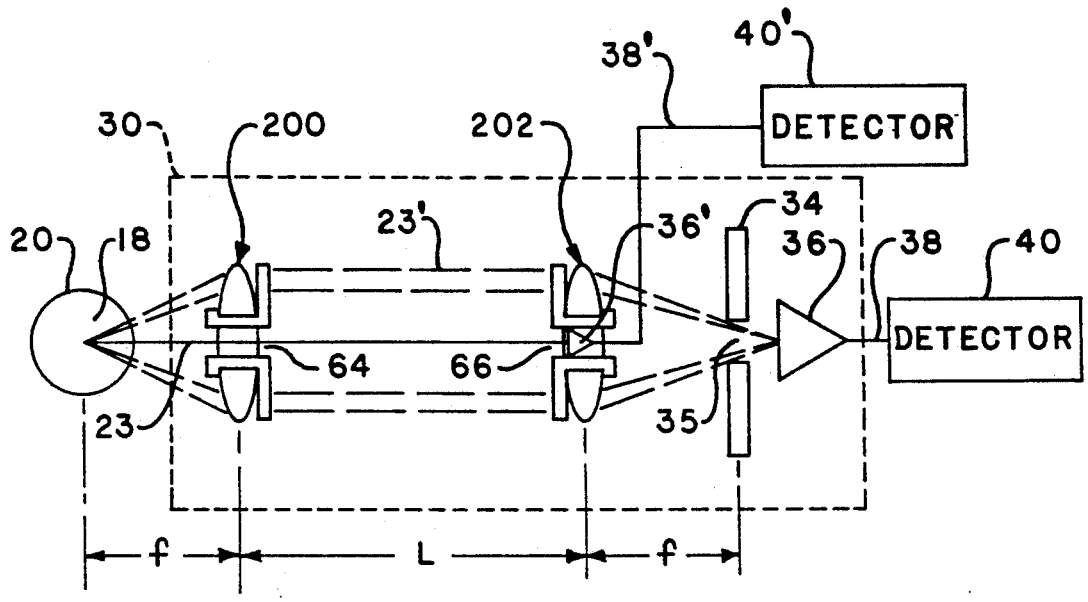
FIG. 13 is a depiction of an optical train incorporating the optical masking element of the present invention.

Thus constructed, the lens 70 with lens insert elements 212 and 50 properly engaged therein constitutes the novel optical element of this invention that is illustrated as 200 and 202 in FIG. 13.

Figure 17:
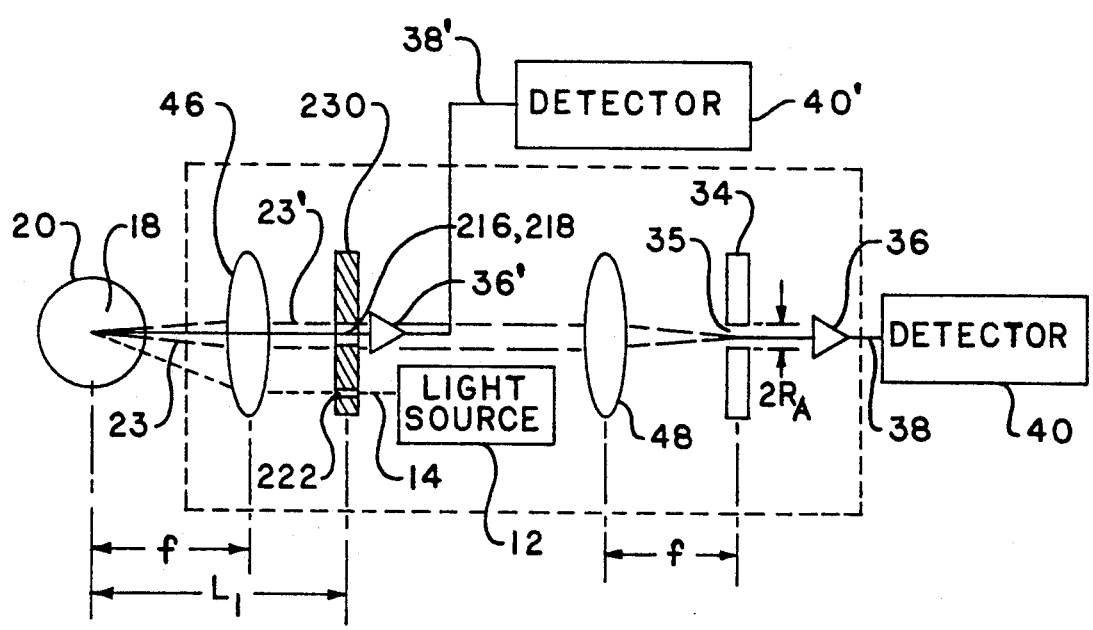
FIG. 17 is a depiction of an alternate embodiment of the optical train of FIG. 13.

It will also be appreciated that the novel masking device represented by the combination of insert elements 212 and 50 may also have application separate from the centrally-bored lens 70 in presenting another novel optical train of the type illustrated in FIG. 17. This optical train 30 will be immediately recognized as having a similarity to the "double-lens" optical train of FIG. 4. In such an optical train 30, the scattered light beam 23 originates within the sample 18, which sample is contained in the sample cell 20. Optical train 30 is aligned with the scattered light beam 23 such that the light beam 23 encounters a first lens 46 at a distance one focal length from the origin of the light scattering. Elementary optics requires that such light entering the lens will not refocus of itself, and will, instead, be split into a plurality of beams 23' parallel to light axis 23. At a distance $L_1$ from the scattering source, the plurality of beams encounters a masking element 230 comprised of insert elements 212 and 50, centered on the light axis 23. This masking element 230 will exclude all beams 23' from lens 46 that are not within the area of the two slits 216 and 218 on element 212. That is to say, all beams 23' that are not between $R_1$ and $R_2$ from the light axis 23 and that are not displaced less than w/2 from diameter 220 will terminate at masking element 230 and will not reach second lens 48. This second lens 48, located colinear to lens 46, will refocus the plurality of beams 23' reaching it into a single point colinear with the source and at a distance one focal length f further along the light axis 23 from the lens 48. As with FIG. 13, it may be preferred to select lens 46 and 48 so that they are identical in radius and focal length, but variation, particularly with respect to focal length, is certainly within the scope of the invention and within the possession of one of skill in optics. An aperture element 34 is located colinearly along light beam 23 and such a distance f from the lens 37. The aperture element 34, also opaque to light beam 23, has an central aperture 35, of radius $R_{A2}$, disposed therein, and it serves to cut out extrinsic light not originating at the light source. Also colinear with light beam 23 is a light detection means 36, preferably a photodiode or photomultiplier tube (PMT), either of which are conventional, and either of which are used to gather electromagnetic energy in the form of photons and convert said energy into a electrical impulse. Such an impulse can be passed via conventional electrical wiring to a light analyzing means 40 for further analysis.

Even further, the central aperture 64 of masking element 230, which results from use of insert element 50, permits mounting of a light detecting means 36' as in FIG. 5, to collect the light passing directly on light axis 23. This light may be used for determining total intensity, by use of wiring means 38' and detector 40', exactly as in FIG. 5. In this manner, some of the complexity of combining lens and masking elements into a single embodiment are overcome. Also, the use of aperture 222 in relation to light source 12 is illustrated.

Just as the exact size and focal length of the lenses 46 and 48 may be varied, it is also within the scope of use of the present invention to place the masking element 230 between the sample 18 and the first lens 46, provided that the masking element has its size adjusted properly to effectively mask all light which would strike lens 46 but for the masking element and the slits therein. It is believed that the preferred orientation and not the required orientation is illustrated in FIG. 17. Similarly, the use of the central aperture of the optical masking element to provide an opening for a light source 12, thereby providing true 180° $\theta$ back-scatter, is within the scope of the invention as described above.

While in accordance with patent statutes, a preferred embodiment and best mode have been presented, the scope of the invention is not limited thereto, but rather is measured by the scope of the attached claims.

I claim:

1. An optical train for simultaneously measuring the intensity and fluctuations of a light beam scattered by a sample contained in a sample cell, said train being disposed upon a base to move smoothly in an arc coplanar to the scattered light beam and receive the light beam along a longitudinal axis thereof, said train comprising in this order from the end of said train which receives said scattered light beam;

a first focusing lens having a radius $R_L$ and focal length f;

an optical masking element comprising a generally flat disc comprising material that is opaque to said light beam, said disc having a radius $R_m$ extending outwardly from a center, said radius being at least as large as the radius $R_L$; said disc further having first and second identical slits disposed symmetrically and radially outwardly from said center on a single diameter, said first slit on a first side of said center and said second slit on the other side of said center, said first and second slits having a first end at a radius $R_1$ from said center and a second end at a radius $R_2$ from said center $R_2$ being larger than $R_1$, said first and second slits also having a width w;

a second focusing lens, having a radius at least as large as $R_L$ and a focal length f';

aperture element comprising an opaque plate with an aperture of radius $R_A$ bored concentrically therethrough;

first light detecting means; and first light analyzing means;

said first focusing lens, optical masking element, second focusing lens, aperture element and first light detecting means being disposed colinearly, in that order, upon the base along the axis of the scattered light beam, such that each is centered upon the light beam, the first focusing lens being located one focal length f from the center of the sample cell, said optical masking element being between said first and second focusing lenses, the second focusing lens being one focal length f' ahead of the aperture element, and the first light detecting means being proximate to the aperture element;

said first light detecting means communicated to said first analyzing means by electrical wiring means, irrelevant of whether said first analyzing means is disposed upon said base.

2. The optical train of claim 1 wherein said first and second focusing lenses are identical in radius $R_L$ and focal length f.

3. The optical train of claim 1 wherein the optical element further has an eccentrically centered aperture.

4. The optical train of claim 3 wherein the eccentric aperture is located on a diameter of said disc that is perpendicular to the diameter on which said slits are disposed.

5. The optical train of claim 1 wherein the disc has a central aperture with radius less than $R_1$ centered at the center of said disc.

6. The optical train of claim 5 wherein said central aperture is adapted for having a second light detecting means positioned therein.

7. The optical train of claim 6 wherein a second light detecting means is positioned in said central aperture.

8. The optical train of claim 7 wherein said second light detecting means is communicated to a second analyzing means by electrical wiring means, irrelevant of whether said second analyzing means is disposed upon said base.

9. The optical train of claim 1 wherein the optical masking element further is provided with means for attachment to said first focusing lens.

10. The optical train of claim 1 wherein a second optical masking element is provided and attached to said second focusing lens.

11. A method for simultaneously acquiring total intensity and fluctuation light scattering data, said method comprising:
 causing a light beam to be emitted from a light source and to pass into a sample contained within a sample cell;
 aligning an optical train having first and second light detecting means, at a fixed angle $\theta$ from the incident axis of said light beam;
 collecting simultaneously total intensity light data in the second light detecting means and fluctuation light data in the first light detecting means;
 communicating simultaneously said total intensity light data and said fluctuation light data via electrical wiring means to respective second and first light analyzing means; and
 analyzing simultaneously said total intensity light data and said fluctuation light data in respective second and first light analyzing means;
wherein said optical train is disposed upon a base to move smoothly in an arc coplanar to the scattered light beam and receive the light beam along a longitudinal axis thereof, and comprises in this order from the end of said train which receives said scattered light beam;
 a first focusing lens having a radius $R_L$ and focal length f;
 an optical masking element comprising a generally flat disc comprising material that is opaque to said light beam, said disc having a radius $R_M$ extending outwardly from a center, said radius being at least at large as the radius $R_L$; said disc further having first and second identical slits disposed symmetrically and radially outwardly from said center on a single diameter, said first slit on a first side of said center and said second slit on the other side of said center, each said slit having a first end at a radius $R_1$ from said center and a second end at a radius $R_2$ from said center, $R_2$ being larger than $R_1$, each said slit also having a width w and the disc has a central aperture with radius less than $R_1$ centered at the center of the disc, said central aperture having a second light detecting means positioned therein;
 a second focusing lens, having a radius at least as large as $R_L$ and a focal length f';
 an aperture element comprising an opaque plate with an aperture of radius $R_A$ bored concentrically therethrough;
 first light detecting means; and
 first light analyzing means;
 said first focusing lens, optical masking element, second focusing lens, aperture element and first light detecting means being disposed colinearly, in that order, upon the base along the axis of the scattered light beam, such that each is centered upon the light beam, the first focusing lens being located one focal length f from the center of the sample cell, said optical masking element being between said first and second focusing lenses, the second focusing lens being one focal length f' ahead of the aperture element, and the first light detecting means being proximate to the aperture element;
 said first and second light detecting means communicated to respective said first and second analyzing means by electrical wiring means, irrelevant of whether said first or second analyzing means is disposed upon said base.

12. The method of claim 11, wherein the light source is a laser.

13. The method of claim 12, wherein the optical masking element has an eccentric aperture located on a diameter of said disc that is perpendicular to the diameter on which said slits are disposed and through which said light beam is directed outwardly through said first focusing lens to said sample cell, so that said fixed angle $\theta$ is near 180°.

14. The method of claim 11, wherein no index matching fluid is used with the sample cell to eliminate wall effects.

15. A method for acquiring fluctuation light scattering data at an angle $\theta$ of 180°, said method comprising:
 aligning an optical train having a first light detecting means, an optical masking element with a central aperture and a first light analyzing means, with a sample contained within a sample cell;
 causing a light beam to be emitted from a light source positioned in the central aperture of the optical masking element of the optical train to pass outwardly of said optical train into said sample, whereafter some of said light is backscattered at an angle of 180° into said optical train;
 collecting said backscattered light as fluctuation light data in the first light detecting means; communicating said fluctuation light data via electrical wiring means to said first light analyzing means; and
 analyzing said fluctuation light data in said first light analyzing means;
 wherein the optical train is disposed upon a base to move smoothly in an arc coplanar to the scattered light beam and receive the light beam along a longitudinal axis thereof, and comprises in this order from the end of said train which receives said scattered light beam;
 a). a first focusing lens having a radius $R_L$ and focal length f;
 b). an optical masking element comprising a generally flat disc comprising material that is opaque to said light beam, said disc having a radius $R_M$ extending outwardly from a center, said radius being at least at large as the radius $R_L$; said disc further having first and second identical slits disposed symmetrically and radially outwardly from said center on a single diameter, said first slit on one side of said center and said second slit on the other side of said center, said first and second slits having a first end at a radius $R_1$ from said center and a second end at a radius $R_2$ from said center, $R_2$ being larger than $R_1$, first and second slit also having a width w and a central aperture with radius less than $R_1$ centered at the center of said disc;

c). a second focusing lens, having a radius at least as large as $R_L$ and a focal length $f'$;

d). an aperture element comprising an opaque plate with an aperture of radius $R_A$ bored concentrically therethrough;

e). first light detecting means; and f). first light analyzing means;

said first focusing lens, optical masking element, second focusing lens, aperture element and first light detecting means being disposed colinearly, in that order, upon the base along the axis of the scattered light beam, such that each is centered upon the light beam, the first focusing lens being located one focal length f from the center of the sample cell, said optical masking element being between said first and second focusing lenses, the second focusing lens being one focal length f' ahead of the aperture element, and the first light detecting means being proximate to the aperture element;

said first light detecting means communicated to said first analyzing means by electrical wiring means, irrelevant of whether said first analyzing means is disposed upon said base.

* * * * *